(12) United States Patent
Shoelson

(10) Patent No.: US 6,630,312 B2
(45) Date of Patent: Oct. 7, 2003

(54) METHOD FOR IDENTIFYING COMPOUNDS FOR TREATMENT OF INSULIN RESISTANCE

(75) Inventor: Steven Shoelson, Natick, MA (US)

(73) Assignee: Joslin Diabetes Center, Inc., Boston, MA (US)

(*) Notice: Subject to any disclaimer, the term of this patent is extended or adjusted under 35 U.S.C. 154(b) by 4 days.

(21) Appl. No.: 09/776,432

(22) Filed: Feb. 2, 2001

(65) Prior Publication Data

US 2001/0036625 A1 Nov. 1, 2001

Related U.S. Application Data

(63) Continuation-in-part of application No. 09/636,150, filed on Aug. 10, 2000, now Pat. No. 6,468,755
(60) Provisional application No. 60/148,037, filed on Aug. 10, 1999.

(51) Int. Cl.[7] .................. G01N 33/53; C12N 11/00; A61K 38/00
(52) U.S. Cl. .................. 435/7.1; 435/7.8; 435/174; 514/2
(58) Field of Search .................. 435/7.1, 7.8, 7.92, 435/174; 514/2

(56) References Cited

U.S. PATENT DOCUMENTS

| | | | |
|---|---|---|---|
| 5,759,787 A | 6/1998 | Strulovici | |
| 5,776,717 A | 7/1998 | Cao | |
| 5,843,721 A | 12/1998 | Rothe et al. | |
| 5,844,073 A | 12/1998 | Rothe et al. | |
| 5,851,812 A | 12/1998 | Goeddel et al. | |
| 5,854,003 A | 12/1998 | Rothe et al. | |
| 5,916,760 A | 6/1999 | Goeddel et al. | |
| 5,932,425 A | 8/1999 | Alkalay et al. | |
| 5,939,302 A | 8/1999 | Goeddel et al. | |
| 5,972,674 A | 10/1999 | Mercurio et al. | |

FOREIGN PATENT DOCUMENTS

| | | |
|---|---|---|
| WO | WO 98/08955 | 3/1998 |
| WO | WO 98/37228 | 8/1998 |
| WO | WO 99/01541 | 1/1999 |

OTHER PUBLICATIONS

Newman et al., "Aspirin Causes Tissue Insensitivity to Insulin in Normal Man", *Journal of Clinical Endocrinology and Metabolism*, 57:1102–1106, 1983.
Rothwarf et al., "IKK–$\gamma$ is an essential regulatory subunit of the IkB kinase complex", *Nature*, 395–297–300, Sep., 1998.
Steinberg, "Meeting Report of the ASPET–Ray Fuller Symposium: Insulin Resistance in Diabetes and Hypertension: Syndrome X and Beyond", *The Journal of Pharmacology and Experimental Therapeutics*, 294:402–406, Apr. 2000.
Yin et al. "The anti–inflammatory agents aspirin and salicylate inhibit the activity of I(kappa)B kinase–beta", 396(6706):77–80, 1998. Nature.

*Primary Examiner*—Elizabeth Kemmerer
*Assistant Examiner*—Regina M. DeBerry
(74) *Attorney, Agent, or Firm*—Fish & Richardson PC

(57) ABSTRACT

The invention features a method of identifying, evaluating or making a compound or agent, e.g., a candidate compound or agent, for treatment of a disorder characterized by insulin resistance. The method includes evaluating the ability of a compound or agent to bind IKK-$\beta$ or modulate IKK-$\beta$ activity, to thereby identify a compound or agent for the treatment of a disorder characterized by insulin resistance. The invention also features compounds for treating insulin resistance identified by such methods, and methods of treating a subject having a disorder characterized by insulin resistance by administering such agents.

9 Claims, 2 Drawing Sheets

METHOD FOR IDENTIFYING COMPOUNDS FOR TREATMENT OF INSULIN RESISTANCE

CROSS-REFERENCE TO RELATED APPLICATIONS

This application is a continuation-in-part application of and claims priority to U.S. application Ser. No. 09/636,150, now U.S. Pat. No. 6,468,755 filed on Aug. 10, 2000, and U.S. Provisional Application Ser. No. 60/148,037, filed Aug. 10, 1999, the contents of which are incorporated herein by reference.

BACKGROUND

Insulin resistance refers to a decreased capacity of circulating insulin to regulate nutrient metabolism. Individuals with insulin resistance are predisposed to developing Type 2 diabetes, and insulin resistance is an integral feature of its pathophysiology. Greater than normal levels of insulin are secreted to overcome target tissue resistance, which leads to the eventual failure of pancreatic β cells in predisposed individuals.

Insulin resistance also occurs in hypertension, cardiovascular disease and dyslipidemia, suggesting an etiologic relationship that is referred to as the metabolic syndrome or syndrome X. The prevalence of insulin resistance is remarkably high, particularly in ageing adult populations (National Diabetes Data Group, *Diabetes in America* (National Institutes of Diabetes and Digestive Diseases, National Institutes of Health, USA, 1994), and rising—most rapidly in the young (Mokdad et al. (2000) *Diabetes Care* 23:1278–1283). Nevertheless, only rare genetic causes have been identified. Environmental factors, including sedentary lifestyle, obesity, and increased age induce insulin resistance, whereas exercise and weight loss reverse it.

SUMMARY

The present invention is based, in part, on the discovery that aspirin reverses insulin resistance in liver and fat cells, e.g., by targeting IKK-β. It has been discovered that insulin sensitivity is improved in vivo by modulating, e.g., reducing, IKKβ activity, e.g., by decreased protein expression. Thus, IKK-β is a target for identifying compounds for the treatment of disorders associated with insulin resistance.

Accordingly, in one aspect, the invention features a method of identifying, evaluating or making a compound or agent, e.g., a candidate compound or agent, for treatment of a disorder characterized by insulin resistance. The method includes evaluating the ability of a compound or agent to interact with, e.g., bind, IKK-β, to thereby identify a compound or agent for the treatment of a disorder characterized by insulin resistance.

In a preferred embodiment, the disorder is diabetes, e.g., Type I or Type II diabetes; hyperglycemia; hyperinsulinemia; dyslipidemia; obesity; polycystic ovarian disease; hypertension, cardiovascular disease, or syndrome X.

In a preferred embodiment, the compound is: a polypeptide, e.g., a randomly generated polypeptide which binds IKK-β; an antibody, e.g., an intrabody or a randomly generated antibody which binds IKK-β or modulates IKK-β activity; a small molecule, e.g., a small molecule which binds IKK-β or modulates IKK-β activity.

In a preferred embodiment, the method further includes contacting the identified compound with IKK-β, e.g., purified IKK-β, to thereby evaluate the interaction, e.g., binding, between the compound and IKK-β.

In a preferred embodiment, the method further includes contacting the identified compound with a cell, e.g., a fat cell or a liver cell, to thereby evaluate the effect of the compound on an IKK-β activity of the cell. The compound can be evaluated based on one or more of: the ability of the compound to modulate, e.g., reduce or reverse, insulin resistance in a cell; the ability of the compound to modulate glucose and/or lipid homeostasis; the ability of the compound to modulate phosphorylation, e.g., of a component of the insulin signaling cascade (e.g., the ability to increase tyrosine phosphorylation of a component of the insulin signaling cascade and/or decrease Ser/Thr phosphorylation of a component of the insulin signaling cascade).

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In another aspect, the invention features a method of identifying a compound or agent for treatment of a disorder characterized by insulin resistance. The method includes contacting IKK-β, or a cell expressing IKK-β with a test compound; and determining whether the test compound interacts with, e.g., binds to IKK-β, and/or modulates the activity of IKK-β, to thereby identify a compound.

Methods for identifying a compound or an agent can be performed, for example, using a cell free assay. For example, the IKK-β can be immobilized to a suitable substrate, e.g., glutathoine sepharose beads or glutathoine derivatized microtitre plates, using a fusion protein which allows for IKK-β to bind to the substrate, e.g., a glutathoine-S-transferase/IKK-β fusion protein.

In a preferred embodiment, the ability of a test compound to bind IKK-β can be determined by detecting the formation of a complex between IKK-β and the compound. The presence of the compound in complex indicates the ability to bind IKK-β.

In a preferred embodiment, IKK-β is further contacted with aspirin.

In another preferred embodiment, a compound is identified using a cell based assay. These methods include identifying a compound based on its ability to modulate, e.g., inhibit, an IKK-β activity of the cell. For example, the ability of a compound to modulate one or more of, e.g., glucose and/or lipid homeostasis, insulin resistance in a cell, e.g., a fat cell or a liver cell, and/or phosphorylation of a component of the insulin signaling cascade can be determined.

In a preferred embodiment, the method further includes contacting the identified compound with IKK-β, e.g., purified IKK-β, to thereby evaluate binding between the compound and IKK-β.

In a preferred embodiment, the method further includes contacting the identified compound with a cell, e.g., a fat cell or a liver cell, to thereby evaluate the effect of the compound on an IKK-β activity of the cell. For example, the ability of a compound to modulate one or more of, e.g., glucose and/or lipid homeostasis, insulin resistance in a cell, e.g., a fat cell or a liver cell, and/or phosphorylation of a component of the insulin signaling cascade can be evaluated.

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In a preferred embodiment, the compound is: a polypeptide, e.g., a randomly generated polypeptide which interacts with, e.g., binds, IKK-β; an antibody, e.g., an intrabody or a randomly generated antibody which interacts with IKK-β; a small molecule, e.g., a small molecule which interacts with IKK-β.

In a preferred embodiment, the compound is a compound other than aspirin.

In a preferred embodiment, the disorder is diabetes, e.g., Type I or Type II diabetes; hyperglycemia; hyperinsulinemia; dyslipidemia; obesity; polycystic ovarian disease; hypertension; cardiovascular disease; or syndrome X.

In another aspect, the invention features a method of identifying a compound or agent for treatment of diabetes, e.g., Type I or Type II diabetes. The method includes contacting IKK-β, or a cell expressing IKK-β, with a test compound; and determining whether the test compound binds to IKK-β, to thereby identify a compound for treatment of diabetes.

Methods for identifying a compound or an agent can be performed, for example, using a cell free assay. For example, the IKK-β can be immobilized to a suitable substrate, e.g., glutathoine sepharose beads or glutathoine derivatized microtitre plates, using a fusion protein which allows for IKK-β to bind to the substrate, e.g., a glutathoine-S-transferase/IKK-β fusion protein.

In a preferred embodiment, the ability of a test compound to bind IKK-β can be determined by detecting the formation of a complex between IKK-β and the compound. The presence of the compound in complex indicates the ability to bind IKK-β.

In a preferred embodiment, IKK-β is further contacted with aspirin.

In another preferred embodiment, a compound is identified using a cell based assay. These methods include identifying a compound based on its ability to modulate, e.g., inhibit, an IKK-β activity of the cell. For example, the ability of a compound to modulate one or more of, e.g., glucose or lipid homeostasis, insulin resistance in a cell, e.g., a fat cell or a liver cell, and/or phosphorylation of a component of the insulin signaling cascade can be determined.

In a preferred embodiment, the method further includes contacting the identified compound with IKK-β, e.g., purified IKK-β, to thereby evaluate binding between the compound and IKK-β.

In a preferred embodiment, the method further includes contacting the identified compound with a cell, e.g., a fat cell or a liver cell, to thereby evaluate the effect of the compound on an IKK-β activity of the cell. For example, the ability of a compound to modulate one or more of, e.g., glucose and/or lipid homeostasis, insulin resistance in a cell, e.g., a fat cell or a liver cell, and/or phosphorylation of a component of the insulin signaling cascade.

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In a preferred embodiment, the compound is: a polypeptide, e.g., a randomly generated polypeptide which interacts with, e.g., binds, IKK-β; an antibody, e.g., an intrabody or a randomly generated antibody which interacts with IKK-β; a small molecule, e.g., a small molecule which interacts with IKK-β.

In a preferred embodiment, the compound is a compound other than aspirin.

In another aspect, the invention features a method of identifying a compound for treatment of a disorder characterized by insulin resistance, e.g., Type I or Type II diabetes; hyperglycemia; hyperinsulinemia; dyslipidemia; obesity; polycystic ovarian disease; hypertension; cardiovascular disease; or syndrome X. The method includes administering a test compound to a cell, and evaluating the ability of the test compound to modulate, e.g., reduce or increase, IKK-β activity in the cell.

In a preferred embodiment, the test compound reduces IKK-β activity.

In a preferred embodiment, the ability of the test compound to modulate IKK-β activity is evaluated by assessing the activity, e.g., the phosphorylation state, of one or more component(s) in the insulin signaling cascade, e.g., insulin receptor (IR), insulin-receptor substrate (IRS) proteins, PI 3-kinase, 3-phosphoinositide-dependent protein kinase-1 (PDK1), and/or AKT kinase. For example, the phosphorylation state, e.g., the tyrosine or Ser/Thre phosphorylation state, of any of IR, IRS, P13, PDK1, or AKT, can be evaluated before, during and/or after treatment of the cell with the test compound.

In a preferred embodiment, the ability of the test compound to modulate IKK-β activity is evaluated by assessing one or more of: insulin receptor (IR) or insulin-receptor substrate (IRS) phosphorylation, e.g., Tyrosine phosphorylation or Ser/Thr phosphorylation.

In a preferred embodiment, the ability of the test compound to reduce Ser/Thr phosphorylation is evaluated.

In another preferred embodiment, the ability of the test compound to increase tyrosine phosphorylation is evaluated.

In another preferred embodiment, a compound is identified using a cell based assay. These methods include identifying a compound based on its ability to modulate, e.g., reduce, an IKK-β activity of the cell. For example, the ability of a compound to modulate, e.g., reduce or reverse serine/threonine phosphorylation of a component of the insulin signaling cascade in a cell, e.g., a fat cell or a liver cell, can be determined.

In another preferred embodiment, the ability of a compound to modulate, e.g., increase, tyrosine phosphorylation of a component of the insulin signaling cascade in a cell, e.g., a fat cell or liver cell, can be determined.

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In another aspect, the invention features a method of treating a subject having a disorder characterized by insulin resistance. The method includes administering a compound or agent which interacts with, e.g., binds, IKK-β, and/or modulates IKK-β activity, to thereby treat the disorder.

In a preferred embodiment, the disorder is diabetes, e.g., Type I or Type II diabetes; hyperglycemia; hyperinsulinemia; dyslipidemia; obesity; polycystic ovarian disease; hypertension; cardiovascular disease; or syndrome X.

In a preferred embodiment, the compound is: a compound other than aspirin; a polypeptide, e.g., a randomly generated polypeptide which interacts with IKK-β; an antibody, e.g., an intrabody or a randomly generated antibody which interacts with IKK-β; a small molecule, e.g., a small molecule which interacts with IKK-β; or combinations thereof. In a preferred embodiment, the method includes administering a nucleic acid encoding one of the above-described compounds. In a preferred embodiment, the compound is a compound identified by a method described herein.

In a preferred embodiment, the compound is administered parenterally, e.g., intravenously, intradermally, subcutaneously, orally (e.g., inhalation). In a preferred embodiment, the administration of the compound is time-released.

In a preferred embodiment, the subject is a human. In another preferred embodiment, the subject is a NOD mouse, an ob/ob mouse, a db/db mouse, a Zucker fatty rat, or a streptozotocin induced rat.

In another aspect, the invention features a method of treating a subject having diabetes, e.g., Type I or Type II diabetes. The method includes administering to a subject a compound or agent which interacts with, e.g., binds, or modulates an activity of IKK-β, to thereby treat the diabetes.

In a preferred embodiment, the compound is: a compound other than aspirin; a polypeptide, e.g., a randomly generated polypeptide which interacts with IKK-β; an antibody, e.g., an intrabody, e.g., an anti-IKK-β antibody or a randomly generated antibody which interacts with IKK-β, a small molecule, e.g., a small molecule which interacts with IKK-β; combinations thereof. In a preferred embodiment, the method includes administering a nucleic acid encoding one of the above-described compounds. In a preferred embodiment, the compound is a compound identified by a method described herein.

In a preferred embodiment, the compound is administered parenterally, e.g., intravenously, intradermally, subcutaneously, orally (e.g., inhalation). In a preferred embodiment, the administration of the compound is time-released.

In a preferred embodiment, the subject is a human. In another preferred embodiment, the subject is a NOD mouse, an ob/ob mouse, a db/db mouse, a Zucker fatty rat, or a streptozotocin induced rat.

In another aspect, the invention features compounds for the treatment of disorders characterized by insulin resistance, identified by the methods described herein.

The terms protein, polypeptide and peptide are used interchangeably herein.

A subject, as used herein, refers to a mammal, e.g., a human. It can also refer to an experimental animal, e.g., an animal model for an insulin-related disorder, e.g., a NOD mouse, an ob/ob mouse, a db/db mouse, a Zucker fatty rat, or a streptozotocin induced mouse or rat. The subject can be a human which is at risk for a disorder characterized by insulin resistance. Such disorders include diabetes, e.g., Type I or Type II, obesity, polycystic ovarian disease and syndrome X.

An "activity of IKK-β" can be one or more of: phosphorylation activity, e.g., modulation of Ser/Thr phosphorylation of a component of the insulin signaling cascade and/or modulation of tyrosine phosphorylation of a component of the insulin signaling cascade; binding activity, e.g., binding to a component of the insulin signaling cascade; modulation of glucose and/or lipid homeostasis; modulation of insulin resistance in a cell, e.g., a fat cell or a liver cell.

DETAILED DESCRIPTION OF THE INVENTION

Figure 1:
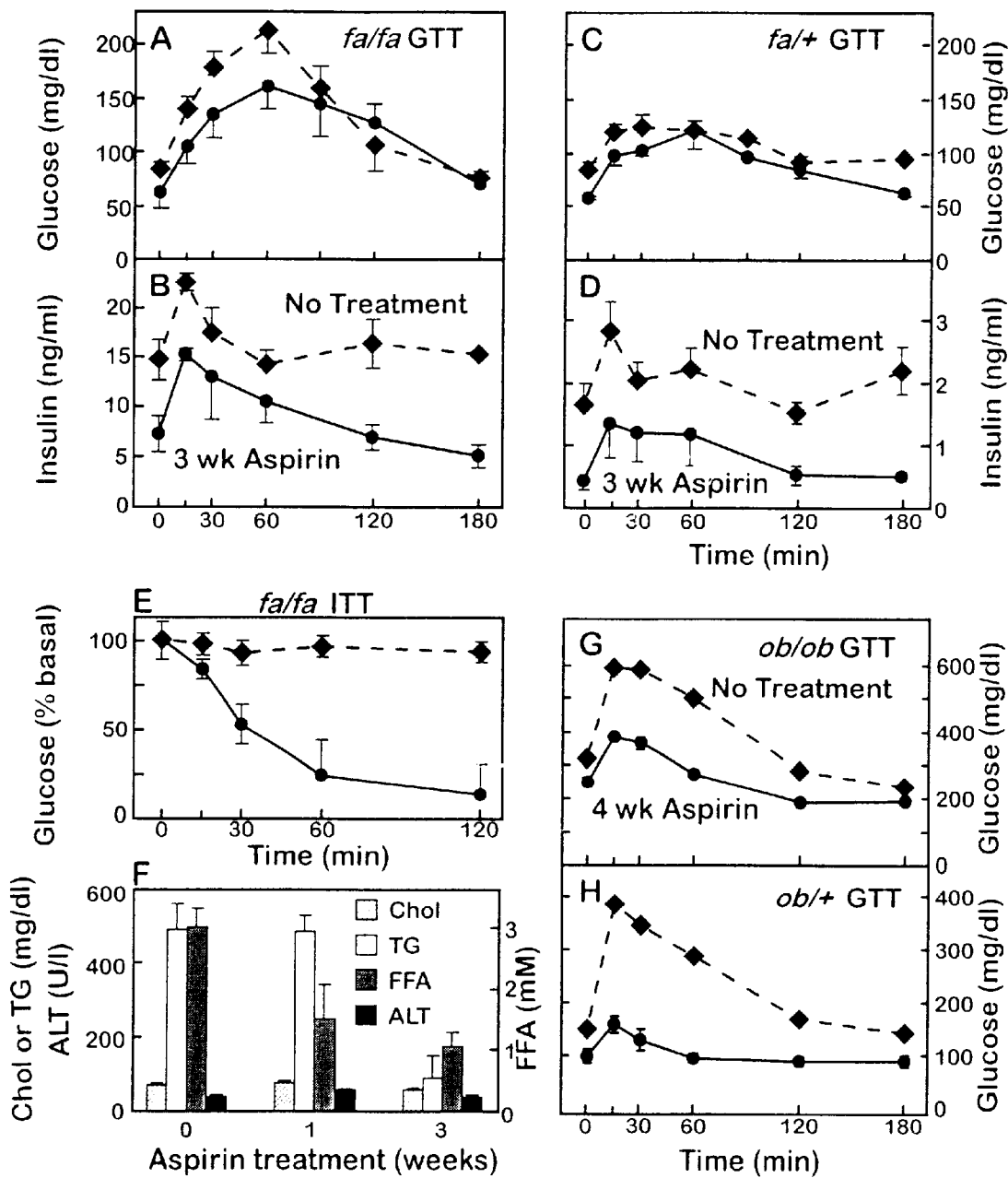
FIGS. 1A–H: In vivo effects of aspirin in Zucker fatty rats and ob/ob mice. (panels A–F) Twelve-week-old male Zucker rats (Harlan) and (panels G,H) eight-week-old ob/ob and ob/+ mice (Jackson Labs) were given free access to food and water. Aspirin (120 mg/kg/day) was continuously infused for 3–4 weeks using Alzet pumps (2ML2 in rats, 2002 in mice) implanted subcutaneously between the scapulae of the animals (all panels: ♦ and dashed line represents control implantation of pump with vehicle only; ● and solid line represents 3 or 4 weeks treatment with aspirin). For glucose tolerance tests (GTT), glucose (2.0 g/kg) was administered by oral gavage (rats) or intraperitoneal injection (mice) after an overnight fast. (panels A,C) Blood glucose and (panels B,D) serum insulin levels were determined during oral glucose tolerance tests in (panels A,B) six Zucker fa/fa rats and (panels C,D) six fa/+ rats. For insulin tolerance tests (ITT) in (panel E) six Zucker fa/fa rats, insulin (2.0 U/kg) was injected intraperitoneally after an overnight fast. (panel F) Cholesterol (Chol), triglyceride (TG), long chain free fatty acid (FFA), and liver alanine aminotransferase (ALT) levels were measured in sera from fasting Zucker fa/fa rats. Glucose tolerance tests were conducted with (panel G) ten ob/ob mice and (panel H) ten ob/+ mice. Data are mean±SEM values; some SEM values are within the area of the symbols.

Primary High-Through-Put Methods for Screening Libraries of Peptide Fragments Various techniques are known in the art for screening gene libraries including existing gene libraries as well as generated mutant gene libraries. Techniques for screening large gene libraries often include cloning the gene library into replicable expression vectors, transforming appropriate cells with the resulting library of vectors, and expressing the genes under conditions in which detection of a desired activity, e.g., in this case, binding to IKK-β, facilitates relatively easy isolation of the vector encoding the gene whose product was detected. Each of the techniques described below is amenable to high through-put analysis for screening large numbers of sequences.

Two Hybrid Systems

Two hybrid (interaction trap) assays can be used to identify peptides which bind IKK-β (see e.g., U.S. Pat. No. 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). These assays rely on detecting the reconstitution of a functional transcriptional activator mediated by protein—protein interactions with a bait protein. In particular, these assays make use of chimeric genes which express hybrid proteins. The first hybrid comprises a DNA-binding domain fused to the bait protein. e.g., IKK-β or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein IKK-β with another protein.

Display Libraries

In one approach to screening assays, the candidate peptides are displayed on the surface of a cell or viral particle, and the ability of particular cells or viral particles to bind IKK-β or a fragment thereof via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140).

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the NH$_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to IKK-β. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Other Methods of Identifying Small Molecules Which Interact with IKK-β

Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to IKK-β. See DesJarlias et al. (1988) *J. Med. Chem.* 31:722; Meng et al. (1992) *J. Computer Chem.* 13:505; Meng et al. (1993) *Proteins* 17:266; Shoichet et al. (1993) *Science* 259:1445. In addition, the electronic complementarity of a molecule to a targeted protein can also be analyzed to identify molecules which bind to the target. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

Secondary Screens

The high through-put assays described above can be followed by secondary screens in order to identify further biological activities which will, e.g., allow one skilled in the art to differentiate agonists from antagonists. For example, a cell based assay can be used to identify compounds which have the ability to modulate, e.g., inhibit, IKK-β activity of a cell. For example, the ability of a compound to modulate one or more of: glucose or lipid homeostasis; insulin resistance in a cell, e.g., a fat cell or a liver cell; and/or phosphorylation of a component of the insulin signaling cascade. Cultured cells which can be used to determine the effect of a compound on insulin resistance include liver and fat cells.

For in vivo testing of a compound to reduce or inhibit insulin resistance, the compound can be administered to an accepted animal model. Insulin resistance can be determined by known methods, such as monitoring glucose tolerance and/or circulating lipid levels. These methods are described in the Examples below.

Experimental models for insulin resistance include NOC mice, ob/ob mice, db/db mice, Zucker fatty rats and streptozotocin induced rats.

Once the core sequence of interest is identified, it is routine to perform for one skilled in the art to obtain analogs and fragments.

EXAMPLES

Example 1

Effects of High-Dose Salicylates in Obese Rodents

A determination of the effects of high-dose salicylates on obese rodents with severe insulin resistance was performed as follows. Twelve-week-old male Zucker fa/fa rats and eight-week-old male ob/ob mice were treated for 3–4 weeks with 120 mg/kg/day of aspirin or salicylate, administered by continuous subcutaneous infusion; this dose is roughly equivalent to 5–10 g/day in humans. Fasting blood glucose values and glucose tolerance were improved in treated Zucker fa/fa rats, compared to untreated controls (FIG. 1, panel A). Concomitant reductions in insulin levels (FIG. 1, panel B) indicated a marked improvement in insulin sensitivity. Zucker fa/fa rats are homozygous for leptin receptor loss-of-function, whereas functional leptin receptor expression is 50% of normal in fa/+ littermates. Glucose tolerance in fa/+ animals was normal, and glucose levels were marginally reduced following aspirin treatment (FIG. 1, panel C). Significantly lower insulin levels in the aspirin-treated group (FIG. 1, panel D) demonstrate improved insulin sensitivity. This occurs even though fa/+ animals have milder insulin resistance. The ability of high-dose aspirin to increase insulin sensitivity was further established using insulin tolerance tests (FIG. 1, panel E). Intraperitoneal insulin (2.0 U/kg) had essentially no effect on blood glucose levels in untreated fa/fa rats, due to severe insulin resistance. The same insulin dose administered to aspirin-treated animals led to dramatic decreases in blood glucose. Type 2 diabetes and insulin resistance are typically associated with abnormalities in circulating lipids. Markedly elevated fasting triglyceride levels in the Zucker rats fell from 494+68 mg/dl to 90±58 mg/dl during three weeks of aspirin treatment (FIG. 1, panel F). Elevated free fatty acid (FFA) levels dropped as well, from 3.1±0.3 mM to 1.1±0.2 mM during the treatment period. The drop in FFA levels occurred within 1 week of aspirin initiation, preceding reductions observed in triglyceride and glucose levels. This is consistent with the hypothesis that elevated FFA levels contribute to the pathogenesis of hyperglycemia and hypertriglyceridemia. Cholesterol levels were unaffected. Hypoglycemia that accompanies salicylate overdose is attributed in some modern medical textbooks to hepatotoxicity; this was not observed, judging from the normal, low serum levels of the liver enzyme alanine aminotransferase (ALT), seen throughout the studies (FIG. 1, panel F). Serum salicylate levels ranged from 0.3–1.3 mM (0.81±0.25 mM). Ob/ob mice are a model for type 2 diabetes, being frankly diabetic in addition to being obese and severely insulin resistant. Fasting blood glucose values and glucose tolerance were significantly improved in aspirin-treated ob/ob mice, compared to untreated controls, at every time point studied (FIG. 1, panel G). Ob/ob mice are leptin deficient. Heterozygous ob/+ mice exhibit postprandial hyperglycemia, but are significantly less insulin resistant. Glucose intolerance in ob/+ mice was normalized with aspirin treatment (FIG. 1, panel H). Neither aspirin nor salicylate affected food intake, blood chemistry, or body weight in Zucker fa/fa rats or ob/ob mice.

Example 2

Analysis of Insulin Signaling Proteins

Tissues were isolated from treated animals and insulin signaling proteins were analyzed. Insulin receptor (IR) tyrosine autophosphorylation, one of the earliest responses to insulin binding, was barely detectable in liver and muscle of insulin resistant Zucker rats. Significantly increased stimulation occurred in corresponding tissues from aspirin- and salicylate-treated animals, signaling an increase in insulin responsiveness. A cascade consisting of insulin receptor (IR), insulin-receptor substrate (IRS) proteins, PI 3-kinase and 3-phosphoinositide-dependent protein kinase-1 (PDK1), is required for maintenance of metabolic homeostasis. Phosphorylation of AKT kinase, a subsequent step in this cascade, paralleled IR activation in tissues from Zucker rats. Insulin-stimulated AKT phosphorylation was weak in liver and muscle of untreated Zucker rats, and increased in tissues after animals were treated with aspirin or salicylate. The reversal of blunted signaling that accompanies high-dose aspirin and salicylate treatment coincides with and may explain the observed increase in in vivo insulin sensitivity.

The electrophoretic mobility of IRS-1 from animal livers increased upon aspirin and salicylate treatment, suggesting a decrease in Ser/Thr phosphorylation. Treatment with alkaline phosphatase increased IRS-1 mobility further and eliminated the differences between samples from treated and control animals. In cultured cells, IRS proteins are especially prone to phosphorylation on serine and threonine residues, which opposes the effect of tyrosine phosphorylation by inhibiting signaling.

Example 3

Role of IKK in Insulin Resistance

Culture cells were used as follows to investigate the mechanisms relating to salicylate treatment to the in vivo reversal of insulin resistance. TNF-α treatment of 3T3-L1 adipocytes induced 'insulin resistance', as judged by significant decreases in insulin-stimulated tyrosine phosphorylation of IR β-subunit (42±11%) and IRS-1 (37±9%). TNF-α mediated 'insulin resistance' was reversed by pretreatment with high-dose (5 mM) aspirin. IR and IRS-1 phosphorylation levels were restored to 126±24% and 136±35%, respectively, compared to untreated controls; IR and IRS-1 protein levels were unchanged in TNF-α and aspirin-treated cells. TNF-α activates a cascade of adapters and kinases, including TRADD, RIP, TRAF2, and TAB1, which act upstream of JNK, p38 MAPK, and the IKK complex. Okadaic acid and calyculin A, two phosphatase inhibitors, also activate IKKβ (DiDonato et al. (1997) *Nature* 388:548; Harhaj & Sun (1997) *J Biol Chem* 272:5409), but without activating upstream elements in the TNF-α signaling cascade. Okadaic acid and calyculin A also induce 'insulin resistance' in isolated tissues and cultured cells (Robinson et al (1993) *Am J Physiol* 265:E36; Paz et al (1997) *J. Biol Chem* 272:29911). Therefore, it was determined whether aspirin would reverse 'insulin resistance' caused by these inhibitors. Marked reductions in insulin-stimulated IR (29±12%) and IRS-1 (16±2%) tyrosine-phosphorylation were prevented by incubating the cells with high-dose aspirin (109±15% and 93±25%, respectively). Notably, the reduced electrophoretic mobility of IRS-1 due to calyculin A-induced phosphorylation was reversed with aspirin, further suggesting that aspirin's ability to reverse insulin resistance might occur through reduced Ser/Thr phosphorylation of components in the insulin signaling cascade.

Hyperglycemia- and hyperinsulinemia-induced insulin resistance in diabetic subjects can be mimicked in cell culture by incubation with high concentrations of glucose and insulin. Potential mechanisms include glucose-induced activation of PKC, which can activate IKK. Since hyperglycemia may simultaneously inhibit insulin signaling and activate NF-κB, it was determined whether high-dose aspirin reversed this type of 'insulin resistance.' Levels of insulin-stimulated IR and IRS-1 tyrosine-phosphorylation were decreased to 47±9% and 18±7% of controls, respectively, in 3T3-L1 adipocytes incubated overnight in media containing 25 mM glucose and 10 nM insulin. Concurrent treatment with aspirin restored IR (107±23%) and IRS-1 (90±23%) tyrosine-phosphorylation to levels seen in cells incubated at 5.5 mM glucose. Blunted signaling was not due solely to inhibition by Ser/Thr phosphorylation, as insulin signaling proteins were 'downregulated' by prolonged treatment with high glucose and insulin. Protein levels were restored by concurrent treatment with aspirin. Serine phosphorylation of IκB leads to ubiquitination and proteosome-mediated degradation. IRS proteins may be degraded by a similar route and in both cases, downregulation was inhibited by aspirin.

Responses to potential mediators of insulin resistance were somewhat different in Fao hepatoma cells, an insulin-responsive model for liver as opposed to fat. TNF-α treatment decreased tyrosine-phosphorylation of IRS-2 (39±9%), a major insulin receptor substrate in liver, but not IR. The decrease was reversed by aspirin (115±31%) and by sodium salicylate (89±8%). Sodium salicylate and aspirin are equipotent inhibitors of IKKβ (Yin et al (1998) *Nature*396:77), whereas aspirin is ~100-fold more potent towards the cyclooxygenases (Furst (1994) *Arthritis Rheum* 31:1–9), suggesting that IKKβ and not COX1 or COX2 mediate these effects. Additional studies evaluated the potential molecular targets of these metabolic effects. Neither ibuprofen nor naproxen, two NSAID inhibitors of COX1 and COX2, reversed TNF-α induced 'insulin resistance'. Similarly, the selective COX2 inhibitor, NS-398, had no effect on TNF-α induced 'insulin resistance.' Studies were conducted with doses of the drugs known to have potent biological effects (Yin et al., supra). These pharmacological profiles further point to IKK as the target of these effects, and demonstrate that COX1 and COX2, the classical targets for NSAIDs, do not mediate the anti-diabetic effects of aspirin and salicylate.

To directly test the potential role of IKK, The IKKα and IKKβ catalytic subunits and NIK, an upstream activator, were expressed in HEK293 cells. Insulin stimulated the activation of IR, IRS-2 and AKT in these cells. Activation was attenuated by expression of IKKβ, IKKα or NIK. Attenuated activation was reversed by treatment with aspirin.

TNF-α does not appear to contribute to insulin resistance in type 2 diabetes and syndrome X, as biological blockers of TNF-α do not alter insulin sensitivity (Ofei et al. (1996) *Diabetes* 45:881; Paquot et al. (2000) *J Clin Endocrinol Metab* 85:1316). However, TNF-α is a potential mediator of acquired insulin resistance (Lang et al. (1992) *Endocrinology* 130:43; Feinstein et al. (1993) *J Biol Chem* 268:26055; Hotamisligil et al. (1993) *Science* 259:87; Hotamisligil et al. (1994) *J Clin Invest* 94:1543). TNF-α activates the IKK complex. TNF-α treatment of untransfected 293 cells reduced insulin-stimulated IR activation to 29±2% of untreated controls. Expression of kinase deficient, dominant inhibitory IKKα(K44A) or IKKβ(K44A) reversed TNF-α-inhibited IR activation. In fact, dominant-inhibitory IKKβ caused a 60% increase in insulin-stimulated IR tyrosine-phosphorylation over controls, whether or not cells had been treated with TNF-α. Similar effects were seen with AKT. TNF-α treatment reduced AKT activation (18±15%), and this was reversed by IKKβ(K44A) expression (174±38%). Active IKK kinases thus mediate 'insulin resistance' in cultured cells, and the inactive kinases act as dominant inhibitors to block TNF-α induced insulin resistance. The consistent ability of dominant-inhibitory IKKβ to elevate IR signaling well above the normal level indicates that IKK inhibits insulin signaling even in the absence of TNF-α. There is in vivo support for this, as well. Fa/+ rats and ob/+ mice (see FIG. 1) and Sprague-Dawley rats that are not insulin resistant, obese, or diabetic, show increased insulin sensitivity in response to aspirin treatment.

Example 4

IKK Transgenic Mice Studies

Figure 2:
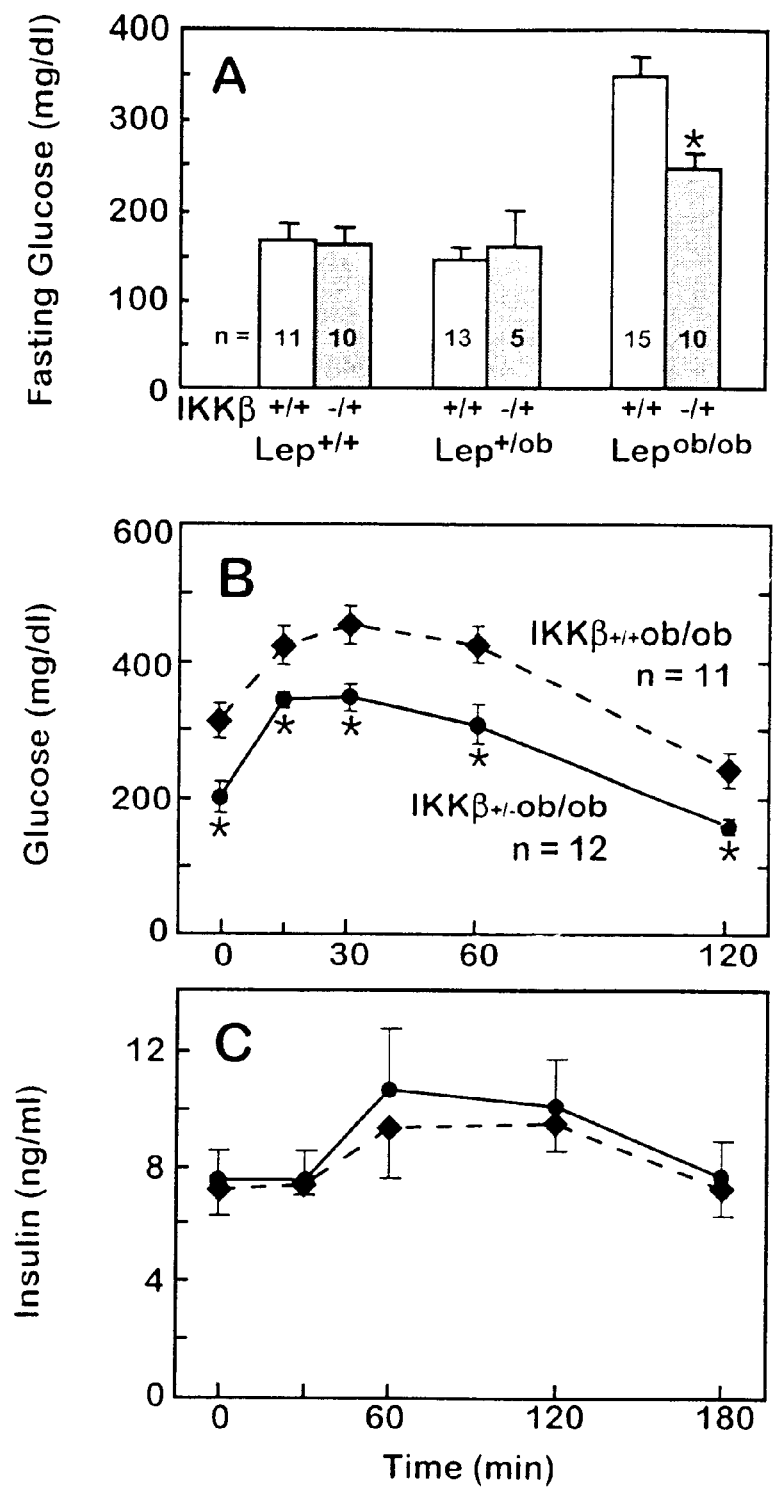
FIGS. 2A–C: Glucose tolerance in IKK-β–/+ob/ob mice. Mice were bred by crossing IKK-β–/+mice (backcrossed 4 generations on C57BL/6J background) with Lep+/ob (C57BLKS) mice (Jackson Labs). F1 offspring were genotyped and doubly heterozygous males were crossed with additional Lep+/ob females. F2 littermates were studied. (A) Fasting blood glucose values are in 6–9 week-old males. *$P<0.003$. (B,C) Glucose tolerance tests were conducted with 9–12 week-old male IKK$^{-/+}$ob/ob and IKK$^{+/+}$ob/ob littermates. Glucose (2.0 g/kg) was administered by intraperitoneal injection after an overnight fast. Blood glucose values are in panel B; plasma insulin concentrations are in panel C. *$P<0.005$; **$P<0.01$; $^{\&}P<0.05$ (Student's t test).

Studies were conducted with mice having targeted disruption of the IKKβ locus. IKKβ−/−mice die in utero (days E12.5 to E14) due to enhanced liver apoptosis (Li et al. (1999) *Science* 284:321–325). However, heterozygous IKKβ+/−mice seem to be normal. IKKβ+/− and Lep-ob/ob mice were crossed to reduce IKKβ gene dose in insulin resistant animals. While there were no significant effects on fasting blood glucose levels in IKKβ+/−Lep+/+ and IKKβ+/−Lepob/+ mice, compared to IKKβ+/+Lep+/+ and IKKβ+/+Lepob/+ littermate controls, fasting blood glucose levels were significantly reduced in IKKβ+/−Lepob/ob mice (248±17 mg/dl), compared to IKKβ+/+Lepob/ob littermates (346±23 mg/dl; P=0.0023) (FIG. 2, panel A). Glucose tolerance in the IKKβ+/−Lepob/ob mice was improved at every time point (FIG. 2, panel B). Insulin levels during the glucose tolerance test were indistinguishable (FIG. 2, panel C), consistent with substantially improved insulin sensitivity in IKKβ+/−Lepob/ob mice compared to IKKβ+/+Lepob/ob littermates. Also consistent with improved metabolic control, plasma free fatty acid levels were lower in the IKKβ+/−Lepob/ob mice (1.86±0.12 mM), compared to IKKβ+/+Lepob/ob littermates (2.24±0.09 g; P=0.029). Despite equivalent caloric intake, weights of the IKKβ+/−Lepob/ob mice (54.1±1.5 g) actually tended to be slightly higher than IKKβ+/+Lepob/ob littermates (51.8±1.4 g; P=0.28), perhaps due to improved glucose utilization and reduced loss of glucose in the urine.

These examples demonstrate that increased IKK activity causes insulin resistance, either when the kinase is overexpressed or activated by known stimulators. Conversely, reducing either IKK activity or expression of its IKKβ subunit significantly improves insulin sensitivity. Even a partial, e.g., 50%, reduction in expression, as occurs in IKKβ$^{+/-}$Lep$^{ob/ob}$ mice, provides a dramatic improvement in insulin sensitivity. These findings indicate that IKK is a valuable new target for drug discovery, e.g., in type 2 diabetes and insulin resistance, because partial inhibition may improve insulin sensitivity without compromising host defenses against infectious agents.

What is claimed:

1. A method of identifying a compound for treatment of insulin resistance, comprising: evaluating the ability of a compound or agent to interact with an IKK-β polypeptide, to thereby identify a compound or agent for the treatment of insulin resistance.

2. The method of claim 1, wherein the ability of the compound or agent to interact with an IKK-β polypeptide is evaluated by evaluating insulin receptor (IR) or insulin receptor substrate (IRS) phosphorylation.

3. The method of claim 2, wherein IR or IRS tyrosine phosphorylation is increased.

4. The method of claim 2, wherein tyrosine phosphorylation of IR or IRS is evaluated.

5. The method claim 2, wherein serine/threonine phosphorylation of IR or IRS is evaluated.

6. The method of claim 2, wherein the test compound or agent is identified if it increases IR or IRS tyrosine phosphorylation.

7. The method of claim 2, wherein the test compound or agent is identified if it reduces IR or IRS serine/threonine phosphorylation.

8. The method of claim 1, wherein the compound is selected from the group consisting of a peptide, an antibody and a small molecule.

9. The method of claim 1, wherein the compound is evaluated by contacting an IKK-β polypeptide with the compound in the presence of aspirin and determining the ability of the compound to bind the IKK-β polypeptide.

* * * * *